United States Patent [19]

Cannata et al.

[11] Patent Number: 5,041,637

[45] Date of Patent: Aug. 20, 1991

[54] PROCESS FOR THE SYNTHESIS OF OPTICALLY ACTIVE AMINOACIDS

[75] Inventors: Vincenzo Cannata, Borgo Nuovo Pontecchio Marconi; Giancarlo Tamerlani, Pontecchio Marconi; Claudio Calzolari, Casalecchio Di Reno, all of Italy

[73] Assignee: Presidenza Del Consiglio Dei Ministri-Ufficio Del Ministro Per Il Coordinamento Delle Iniziatjvo Per La Ricerca Scientifica E Technologica, Italy

[21] Appl. No.: 374,769

[22] Filed: Jul. 3, 1989

[30] Foreign Application Priority Data

Jul. 12, 1988 [IT] Italy .................. 21323 A/88

[51] Int. Cl.$^5$ .................................. C07C 227/30
[52] U.S. Cl. ........................ 562/446; 560/40; 560/39; 558/392; 564/164
[58] Field of Search ............ 560/40, 39; 562/446, 562/401; 558/392; 564/164

[56] References Cited

U.S. PATENT DOCUMENTS

| | | | |
|---|---|---|---|
| 2,388,688 | 11/1945 | Hass .................. | 562/401 |
| 3,422,135 | 1/1969 | Yamada et al. .......... | 562/401 |
| 4,379,941 | 4/1983 | House .................. | 560/39 |
| 4,642,205 | 2/1987 | Aco et al. ............. | 562/401 |

FOREIGN PATENT DOCUMENTS 745  2/1979  European Pat. Off. .......... 562/401

*Primary Examiner*—James H. Reamer
*Attorney, Agent, or Firm*—Samuels, Gauthier & Stevens

[57] ABSTRACT

New process for the synthesis of optically active aminoacids of formula

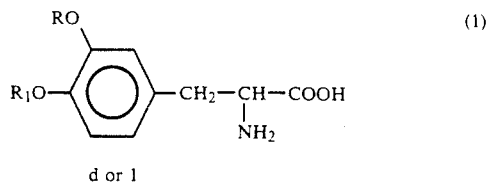

d or l by treating compounds of formula

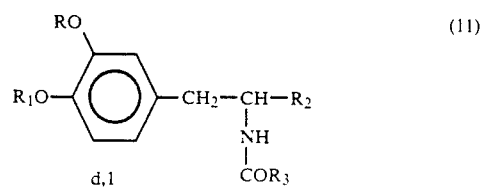

d,l which an optically active alcohol of formula

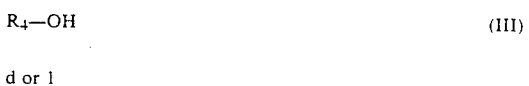

d or l To obtain a pair of diastereoiosmer esters of formula

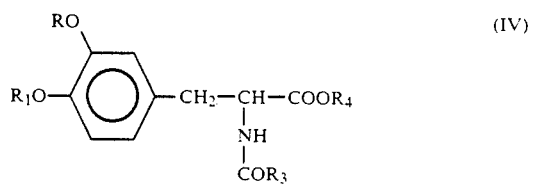

d, d + l, d or d, l + l,l which is resolved in basic medium into the single diastereoisomer esters of formula

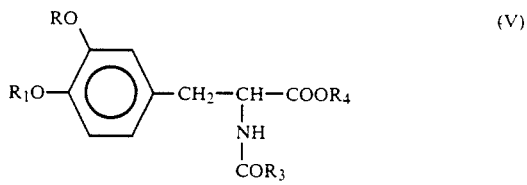

d, d or l, d or d, l or l,l from which the desired optically active aminoacid of formula (I) is obtained by treatment in acid medium.

6 Claims, No Drawings

PROCESS FOR THE SYNTHESIS OF OPTICALLY ACTIVE AMINOACIDS

SUMMARY OF THE INVENTION

New process for the synthesis of optically active aminoacids of formula

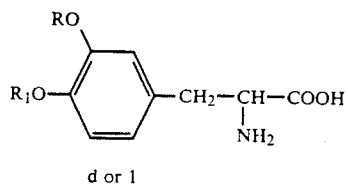

d or l wherein R and $R_1$, equal or different, represent a hydrogen atom or an alkyl radical, straight or branched, containing from 1 to 6 carbon atoms, by reacting compounds of formula

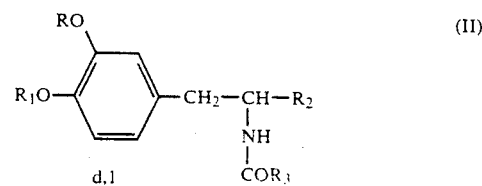

d,l wherein R and $R_1$ have the above seen meanings, $R_2$ represent a nitrile group or a COOH group and $R_3$ represents an alkyl or an alkoxy radical, straight or branched, containing from 1 to 6 carbon atoms or an aryl radical, with an optically active alcohol of formula $$R_4-OH \qquad (III)$$

d or l wherein $R_4$ represents an alkyl or cycloalkyl group, substituted or unsubstituted, containing from 3 to 12 carbon atoms, to obtain a pair of diastereoisomer esters of formula

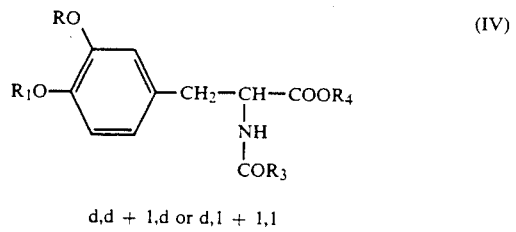

d,d + l,d or d,l + l,l which is resolved in basic medium into the single diastereoisomer esters of formula

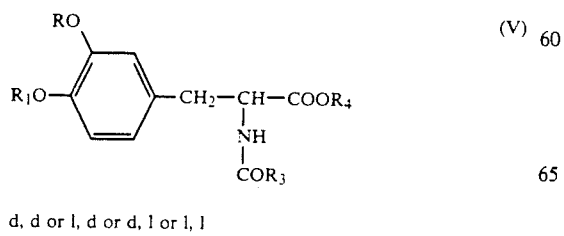

d, d or l, d or d, l or l, l from which the desired optically active aminoacid of formula (I) is obtained by treatment in acid medium.

BACKGROUND OF THE INVENTION

In the nature there are many optically active aminoacids known for their pharmacological properties. It is known that the natural synthesis of these aminoacids brings to aminoacids of L configuration which are endowed of pharmacological activity in man. The (−)-3,4-dihydroxyphenyl-L-alanine, also known as 3-hydroxy-L-tyrosine or as L-(−)-2-amino-3-(3,4-hydroxyphenyl) propanoic acid, which is present in nature in some leguminous plants and which is internationally known as a drug useful in the therapy of the Parkinson's disease under the name of levodopa, has a great importance.

As the chiral syntheses which usually take place in nature are at present difficult to carry out in the field of the chemical synthesis, it is necessary to find methods for the optical resolution of the racemic mixtures of aminoacids or of precursors thereof. A method used for the optical resolution is based on the different chemical-physical properties of diastereoisomer derivatives of the aminoacids themselves, for instance their salts, esters or amides, with an optically active compound.

The different solubility of the two diastereoisomers often makes possible to separate them, under appropriate conditions, by means of a fractionated crystallization.

Harada and Hayakawa Bull. Chem. Soc. Japan, 37, 191, (1964), separated the hydrochlorides of diastereoisomer menthyl esters of some aminoacids by starting the crystallization of a supersaturated solution by means of a diastereoisomer, while Halpern and Westley, Chem. Comm., 421, (1965), similarly separated the paratoluensulfonates of diastereoisomer menthyl esters of aminoacids.

The optical resolution of racemic mixtures of phenylalanine and of phenylglycine is exemplified in U.S. Pat. No. 4,379,941 where it is also named the optical resolution of other aminoacids like 4-hydroxyphenylglycine, 3,4-dihydroxyphenylalanine, tyrosine and tryptophane by means of chromatographic separation on silica gel of diastereoisomer esters coming from the esterification of racemic mixtures of these aminoacids with l-menthol.

All these methods are characterized in that the maximum recovery of product in the optical separation can theoretically reach the 50% of the racemic mixture of the diastereoisomers and, moreover, the process described in U.S. Pat. No. 4,379,941 clearly appears to be a speculative laboratory method without any possibility of an useful industrial exploitation.

The process described in the present invention, on the contrary, is characterized from the very important fact that in theory the whole racemic aminoacid can be transformed into the desired diastereoisomer. Moreover this process is easy to carry out and can be industrially exploited and therefore it is a remarkable progress over the prior art.

DESCRIPTION OF THE INVENTION

The object of the present invention is a new process for the synthesis of optically active aminoacids of formula

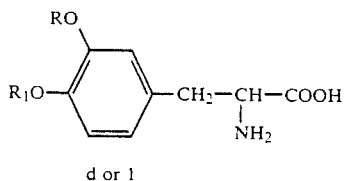

d or l wherein R and $R_1$, equal or different, represent a hydrogen atom or an alkyl radical, straight or branched, containing from 1 to 6 carbon atoms. The methyl, ethyl, isopropyl, propyl, n-butyl, sec-butil, tert-butyl, n-pentyl, isopentyl, neopentyl, tert-pentyl, hexyl and isohexyl radicals are meant as straight or branched alkyl radicals.

The first step of the process is the reaction of compounds of formula

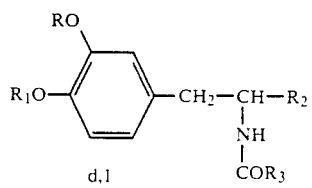

d,l wherein R and $R_1$ have the above seen meanings, $R_2$ represents a nitrile group or a COOH group and $R_3$ represents an alkyl or an alkoxy radical, straight or branched, containing from 1 to 6 carbon atoms, or an aryl radical, with an optically active alcohol of formula $$R_4\text{—OH} \quad (III)$$

d or l wherein $R_4$ represents an alkyl or a cycloalky radical, substituted or unsubstituted, containing from 3 to 12 carbon atoms, in an organic solvent immiscible with water, selected between the alkyl halides containing from 1 to 4 carbon atoms and the aromatic hydrocarbons, optionally in presence of acids or bases. Optically active alcohols which are particularly suitable for the aims of the present invention are optically active cycloalkanols selected from d and l-menthol, d- and l-borneol, d- and l-isomenthol, d- and l-neomenthol, d and l-neoisomenthol, d- and l-1-cyclohexylethanol, d- and l-campholalcohol, d- and l-isoborneol, d- and l-3-methylcyclopentanol. The l-menthol is particularly preferred among the above mentioned optically active alcohols.

In this way, a pair of diastereoisomer esters of formula

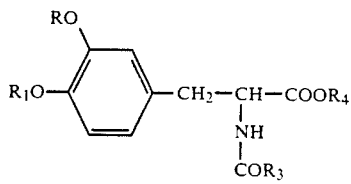

d,d + l,d or d,l + l,l is obtained, wherein R, $R_1$, $R_3$ and $R_4$ have the above seen meanings.

The second step consists in treating said pair of diastereoisomer esters of formula (IV), dissolved in an anhydrous organic solvent, with a strong base selected from an alkaline alcoholate containing from 1 to 6 carbon atoms or an alkaline amide or hydride, preferably under an atmosphere of an inert gas, in order to obtain a single diastereoisomer ester of formula

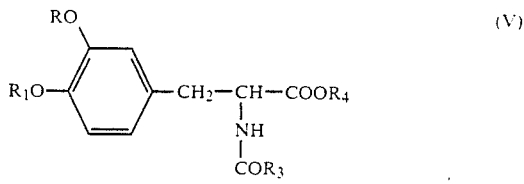

d, d or l, d or d, l or l, l

The third step of the process consists in treating the single diastereoisomer ester of formula (V) by means of aqueous solutions of strong organic or inorganic acids, or mixtures thereof, in order to obtain the optically active aminoacid of formula (I). When one or both R and $R_1$ represent an alkyl radical, straight or branched, containing from 1 to 6 carbon atoms, it is possible to obtain the complete dealkylation by using more drastic conditions of temperature and of time of reaction. In this way the aminoacid of formula (I) wherein $R=R_1=$hydrogen is obtained, which corresponds, in the L-(−) configuration, to the L-(−)-2-amino-3-(3,4-dihydroxyphenyl)propanoic acid, known as levodopa.

The reaction between the compounds of formula (II) and the optically active alcohols of formula (III) to obtain the racemic mixtures of diastereoisomer esters of formula (IV) is carried out in an organic solvent immiscible with water selected from the aliphatic halides containing from 1 to 4 carbon atoms and the aromatic hydrocarbons, toluene being the preferred one presence of acids selected from aqueous or anhydrous sulfuric acid, alkysulfonic or arylsulfonic acids or mixtures thereof, depending on the meaning of $R_2$. So, for istance, when $R_2$ represents a nitrile group, the reaction is carried out in presence of aqueous sulfuric acid, alone or together with an alkylsulfonic or an arylsulfonic acid, at the boiling temperature of the reaction mixture, for a period of time comprised between about 2 and about 6 hours and then going on with the heating to the boiling temperature for a period of time comprised between about 2 and about 4 hour while eliminating the water coming from the reaction by means of an azeotropic distillation. When $R_2$ represents a COOH group, the reaction is catalyzed by sulfuric acid or by alkylsulfonic or arylsulfonic acids, preferably metanesulfonic and p-toluenesulfonic acid, or mixtures thereof, at the boiling temperature of the reaction mixture for a period of time comprised between about 2 and about 12 hours by eliminating the water coming from the reaction by azeotropic distillation.

During the azeotropic distillation the water is separated from the organic solvent through a suitable separator while the organic solvent is continuously recycled. The acid catalyst is eliminated by means of aqueous washings at the end of the reaction.

In this way, pairs of diastereoisomer esters of formula

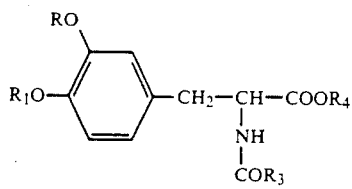

(IV)

d,d + l,d or d,l + l,l are obtained, wherein R, $R_1$, $R_3$ and $R_4$ have the above seen meanings.

These compounds of formula (IV) are new and therefore they are a further object of the present invention. They can be isolated according to known techniques and characterized or they can undergo the subsequent resolution into the single diastereoisomer esters directly in the reaction medium which is previously made anhydrous by treatment with a suitable dehydrating agent selected from anhydrous calcium chloride or sodium sulfate, or by azeotropic distillation. Said resolution is carried out in presence of an organic solvent selected from the alkyl halides containing from 1 to 4 carbon atoms and the aromatic hydrocarbons, preferably toluene, by adding to the reaction mixture an amount of a strong base comprised between about 0.05 and about 0.25 molar equivalents calculated on the pair of diastereoisomer esters of formula (IV).

Said strong base is selected from the alkaline alcoholates containing from 1 to 6 carbon atoms, or from the alkaline amides and hydrides; the potassium tert-butylate is the strong base preferably used. The resulting mixture is kept at a temperature comprised between the room temperature and about 85° C., preferably under an atmosphere of an inert gas like, for instance, nitrogen, for a period of time comprised between about 4 and about 24 hours. During this period of time the crystallization of the desired single diastereoisomer ester starts and it can be helped by seeding the reaction mixture by means of a little amount of the desired diastereoisomer ester.

The crystallization is completed by cooling at a temperature comprised between the room temperature and 0° C.; after filtering and drying, the single diastereoisomer esters of formula

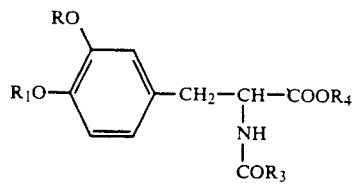

(V)

d, d or l, d or d, l or l, l are obtained, wherein R, $R_1$, $R_3$ and $R_4$ have the above seen meanings. These esters of formula (V) are new and therefore they constitute a further object of the present invention. This process of crystallization in presence of a strong base causes the transformation of the more soluble diastereoisomer ester into the diastereoisomer which crystallizes, so obtaining yields of optical resolution far higher than the theoretical 50%, calculated over the starting pair of diastereoisomer esters, of a normal resolution by fractional crystallization. In fact, as it can be easily deduced from the non limiting examples hereinafter reported, the yields of a single diastereoisomer ester are very high, about 90% calculated over the starting pair of diasteroisomer esters. The compounds of formula (V) are then submitted to hydrolysis under acidic conditions to remove the groups $COR_3$ and $R_4$.

When one or both of R and $R_1$ represent an alkyl, straight or branched, containing from 1 to 6 carbon atoms, it is possible, by operating under more drastic conditions of temperature and of reaction time, to obtain also the complete dealkylation of the compounds of formula (V), so obtaining the aminoacid of formula (I) wherein $R = R_1 =$ hydrogen, which corresponds, in the L-(−) configuration, to the L-(−)-2-amino-3-(3,4-dihydroxyphenyl) propanoic acid, known as levodopa. In practice, the reaction of hydrolysis and the possible accompanying reactions of dealkylation are carried out in acid aqueous medium in presence of aqueous solutions of hydrochloric or hydrobromic acid or of mixtures thereof, at the boiling temperature of the reaction mixture for a period of time comprised between about 4 and about 24 hours, preferably distilling off under a vapour stream the oily layer which forms. The reaction mixture is subsequently cooled, diluted with water, decolourized with active charcoal and filtered over dicalite. The filtrate is brought to pH 4.5 by means of an aqueous concentrated solution of a base and in this way the desired product of formula (I) crystallizes and subsequently it is recovered according to known techniques. The compounds of formula (II) wherein $R_2$ represents a nitrile group and the compounds of formula (IV) and (V) are new and therefore they constitute a further object of the present invention.

The synthesis of the intermediates which bring to the achievement of the compounds of formula (VI) is a further object of the present invention.

The starting product for the synthesis of these intermediates is the aldehyde of formula

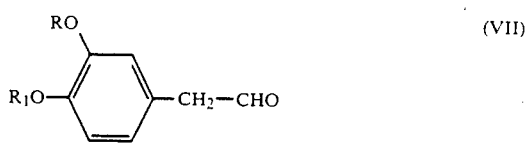

wherein R and $R_1$ represent an alkyl radical, straight or branched, containing from 1 to 6 carbon atoms, from which the desired intermediates can be obtained according to two different ways that are indicated in the following schemes 1, 2 and 3

SCHEME 1

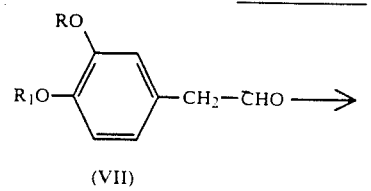

(VII)

SCHEME 1 (continued)
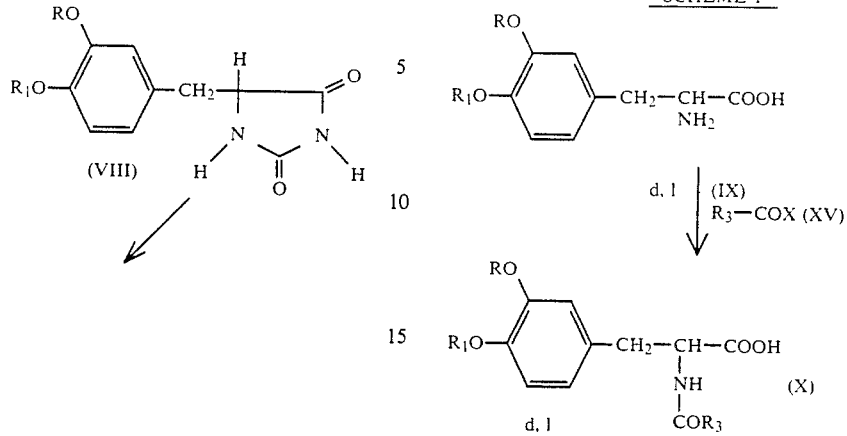
SCHEME 2
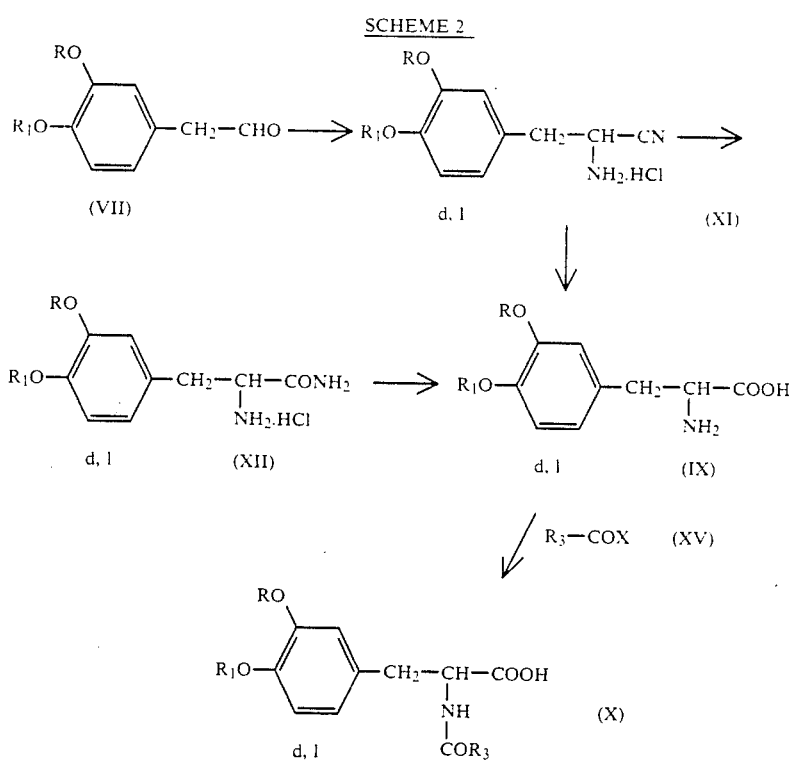
SCHEME 3
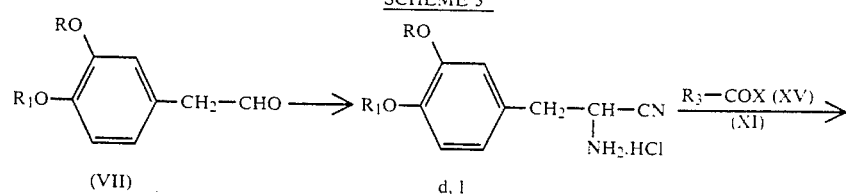

SCHEME 3 -continued

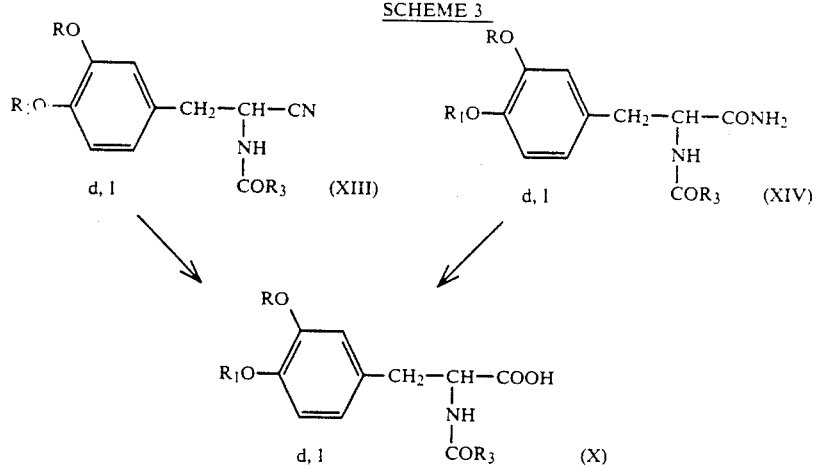

The process according to scheme 1 consists in reacting a molar equivalent of the aldehyde of formula (VII) with about one molar equivalent of an alkaline cyanide, preferably sodium cyanide, with from about 1 to about 2 molar equivalents of ammonium bicarbonate and with from about 0.5 to about 1 molar equivalents of ammonium sulfate in an aqueous solution of ammonium hydroxide, in presence of an organic solvent immiscible with water selected from the alkyl halides containing from 1 to 4 carbon atoms, preferably trichloroethane, in autoclave at a temperature from about 70° C. and about 110° C. for a period of time comprised from about 2 to about 8 hours. The so obtained hydantoin of formula (VIII) is treated with an aqueous solution of an alkaline hydroxide, preferably sodium hydroxide, at the boiling temperature of the reaction mixture for a period of time comprised between about 4 and about 12 hours, so obtaining the aminoacid of formula (IX). This aminoacid is acylated by treatment with a suitable acylating agent of formula

wherein $R_3$ represents an alkyl or alkoxy radical, straight or branched, containing from 1 to 6 carbon atoms or an aryl radical and X represents a halogen atom or a $OCOR_5$ group in which $R_5$ represents a straight or branched alkyl radical containing from 1 to 6 carbon atoms, to give the products of formula (X). The reaction of acylation is preferably carried out without isolating the aminoacid of formula (IX) from the reaction medium and preferably takes place at a temperature comprised from about 0° C. to the room temperature, for a period of time comprised from about 0.5 to about 6 hours at a pH range comprised from about 7 to about 12. The compounds of formula (X) are separated at the end of the reaction by precipitating them at acidic pH, comprised between about 1 and about 3, at a temperature comprised between about 0° C. and the room temperature.

The first step of the process according to scheme 2 regards the preparation of the aminonitrile hydrocloride of formula (XI) by reacting one molar equivalent of the aldehyde of formula (VII) with from about 1 to about 3 molar equivalents of a cyanide of an alkali metal, preferably sodium cyanide, and of ammonium chloride in presence of from about 3 to about 10 molar equivalents of ammoniun hydroxide. The reaction takes place in aqueous solution in presence of an organic solvent immiscible with water selected from the aromatic hydrocarbons and the alkyl halides containing from 1 to 4 carbon atoms, preferably methylene chloride, at a temperature comprised between about 30° C. and about 70° C. for a period of time comprised from about 1 to about 8 hours.

The aminonitrile is extracted from the organic phase by means of an aqueous diluted solution of hydrochloric acid from which the hydrochloride of formula (XI) crystallizes by saturation with gaseous hydrochloric acid or by adding an alkaline chloride or ammonium chloride. The hydrochloride of the propionamide of formula (XII) is obtained by hydrolizing said compound by means of an aqueous solution of hydrochloric acid at a temperature comprised between the room temperature and 50° C. for a period of time comprised from about 2 to about 24 hours.

By treating said propionamide by means of an aqueous solution of hydrochloric acid at a temperature comprised between about 80° C. and about 100° C. for a period of time comprised between about 1 and about 4 hours, the aminoacid of formula (IX) is obtained. This aminoacid, preferably, is not separated but it is acylated in the same reaction medium, as already previously described, by means of a suitable acylating agent of formula $R_3$—COX (XV), wherein $R_3$ and X have the above seen meanings, so obtaining the compounds of formula (X).

The aminoacid of formula (IX) can also be directly obtained from the aminonitrile of formula (XI) without isolating the intermediate amide of formula (XII), by working at temperatures comprised from about 80° C. to about 100° C. for a period of time comprised between about 2 and about 8 hours.

The process according to the scheme 3 envisages the acylation of the hydrochloride of the aminonitrile of formula (XI) with an acylating agent of formula $R_3$—COX (XV), wherein $R_3$ and X have the above seen meanings, to get the compounds of formula (XIII).

The reaction of acylation is preferably carried out in an organic solvent selected from an aromatic hydrocarbon and an alkyl halide containing from 1 to 4 carbon atoms, in presence of an organic tertiary base, preferably triethylamine, for a period of time comprised from about 1 to about 6 hours at a temperature comprised between 0° C. and the room temperature. The reaction mixture is subsequently washed with aqueous acidic and basic solutions and then the compounds of formula (XIII) are isolated by evaporating off under vacuum the organic solvent.

The compounds of formula (XIV) are obtained by treating the compounds of formula (XIII) by means of an aqueous solution of hydrochloric acid at a temperature comprised between about 0° C. and about 30° C. for a period of time comprised between about 0.5 and about 4 hours and by filtering the reaction mixture.

The compounds of formula (XII), (XIII) and (XIV) are new and therefore they constitute a further object of the present invention.

The compounds of formula (XIII) and (XIV) give the compounds of formula (X) by treatment with aqueous solutions of hydrochloric acid at a temperature comprised between 40° C. and 70° C. for a period of time comprised between about 4 and about 12 hours.

The examples described hereinafter are a further illustration of the process object of the present invention but they have not to be considered as an its limitation.

EXAMPLE 1

5-(3,4-dimethoxybenzyl)hydantoin

A mixture of 215 ml of water, 215 ml of a 27% (w/v) aqueous solution of ammonium hydroxide, 35.3 g of sodium cyanide, 113.3 g of ammoniun bicarbonate, 47.5 g of ammonium sulfate and a solution containing 129.6 g of 3.4-dimethoxyphenylacetaldehyde in 900 ml of trichloroethane is heated at 90° C. for 6 hours in an antoclave and then is cooled and filtered.

The organic layer is discarded while the aqueous layer is concentrated under vacuum until complete elimination of the ammonium hydroxide and then it is cooled. The 5-(3,4-dimethoxybenzyl) hydantoin crystallizes and then it is filtered, washed with cold water and dried under vacuum, thus obtaining 122.8 g of product with a yield equal to 69%. A sample is crystallized from acetone and shows m.p.=162°–163° C.

EXAMPLE 2 d,l-N-acetyl-3,4-dimethoxyphenylalanine monohydrate

A mixture of 10 g of 5-(3,4-dimethoxybenzyl)hydantoin and of 20 ml of a 30% (w/v) aqueous solution of sodium hydroxide is heated to the boiling for 7 hours and then it is cooled to room temperature and added with 25 ml of water and 8 ml of 32% (w/v) aqueous solution of hydrochloric acid. 4.5 Ml of acetic anhydride are added to the reaction mixture in about one hour while keeping the temperature at about 10° C. Subsequently the reaction mixture is brought to pH 7 by adding a 32% (w/v) aqueous solution of hydrochloric acid, then it is filtred and the filtrate is acidified till pH 1. The suspension is cooled to 2° C. and then it is filtered. The solid is washed at 50° C. giving 10.5 g of product with a yield of 92%.

EXAMPLE 3 d,l-2-amino-3-(3,4-dimethoxyphenyl)propionitrile hydrochloride

A solution of 63.4 g of 3,4-dimethoxyphenylacetaldehyde in 50 ml of methylene chloride is added in about 30 minutes, while keeping the temperature at about 40° C., to a solution made of 110 ml of water, 220 ml of a 27% (w/v) aqueous solution of ammonium hydroxide, 20.9 g of sodium cyanide and 35.5 g of ammonium chloride. The reaction mixture is kept for 2 hours at 45°÷50° C., then it is cooled to about 25° C. and the two layers are separated. The aqueous layer is twice extracted with 100 ml of methylene chloride and then it is discarded, while the organic layer, containing the nitrile, is extracted with a mixture of 270 ml of water and of 37 ml of 32% (w/v) aqueous hydrochloric acid. The aqueous solution containing the hydrochloride of the aminonitrile is kept under stirring for 12 hours so obtaining the crystallization of the product. The suspension is then saturated with gaseous hydrochloric acid, kept 2 hours under stirring at room temperature and other 2 hours at 10° C. and lastly it is filtered. After drying under vacuum, 67 g of the hydrochloride of the nitrile are obtained with a yield of 78.6%. The product shows a m.p.=191° C. with decomposition.

EXAMPLE 4 d,l-2-amino-3-(3,4-dimethoxyphenyl)propionamide hydrocloride

100 Grams of d,l -2-amino-3-(3,4-dimethoxyphenyl)-propionitrile hydrochloride are suspended in 400 ml of a 32% (w/v) aqueous solution of hydrochloric acid and kept at room temperature for 16 hours and at 45° C. for 30 minutes. The suspension is filtered after cooling to 2° C. and the solid is washed first with 80 ml of a 32% (w/v) cold aqueous solution of hydrochloric acid and then with acetone; subsequently it is dried under vacuum at 40° C. giving 98.7 g of product with a yield of 92%.

EXAMPLE 5 d,l-N-acetyl-3-(3,4-dimethoxyphenyl)alanine monohydrate

26 Grams of d,l-2-amino-3-(3,4-dimethoxyphenyl)-propionamide hydrochloride are suspended in 100 ml of a 32% (w/v) aqueous solution of hydrochloric acid and the reaction mixture is heated at 90° C. for two hours, then it is cooled to room temperature and evaporated to dryness under vacuum. The residue is treated with 250 ml of water, alkalinized to pH 9.5 by means of a 15% (w/v) aqueous solution of sodium hydroxide and the ammonia is evaporated off. Subsequently, 20 ml of acetic anhydride are added in about 1 hour while keeping the pH between 7 and 8.5 by means of a 15% aqueous solution of sodium hydroxide. The pH of the reaction mixture is brought to 2 30 minutes after the end of the addition of the acetic anhydride and after cooling to 0° C. the suspension is filtered. The solid is washed with cold water on the filter and dried under vacuum to give 24.5 g of product with a yield of 86%.

d,l-2-Acetamido-3-(3,4-dimethoxyphenyl)propionitrile 121.4 Grams of d,l-2-amino-3-(3,4-dimethoxyphenyl) propionitrile hydrochloride are suspended in a mixture of 300 ml of water and 300 ml of methylene chloride and the pH is brought to 6.5 by means of a 27% (w/v) aqueous solution of ammonium hydroxide. The layers are separated, the aqueous phase is discarded while the organic phase is dried over anhydrous sodium sulfate, filtered and added with 70 ml of triethylamine. The solution is cooled to about 10° C. and in about 1 hour is added with 52.5 of acetic anhydride and then with 200 ml of water and with 50 ml of a 32% (w/v) acqueous solution of hydrochloric acid. After separating the layers, the aqueous phase is discarded while the organic phase is added with other 200 ml of water and the pH is brought to 9 with a 30% (w/v) aqueous solution of sodium hydroxide. The layers are separated, the aqueous phase is discarded while the organic phase is dried over anhydrous sodium sulfate, filtered and evaporated to dryness. The product obtained is dried under vacuum at 40° C. and shows m.p.=134°÷135° C. 121 Grams of d,l-2-acetamido-3-(3,4-dimethoxyphenyl) propionitrile are obtained with a yield of 97.5%.

EXAMPLE 7 d,l-N-acetyl-3,4-dimethoxyphenylalanine monohydrate

62 Grams of d,l-2-acetamido-3-(3,4-dimethoxyphenyl) propionitrile are added under strong stirring to a 32% (w/v) acqueous solution of hydrochloric acid. The temperature of the reaction mixture goes up till about 55° C. and the suspension completely dissolves. The reaction mixture is kept to this temperature for other 5 hours under stirring, then it is cooled to about 5° C. and is diluted with 200 ml of water. Then 70 ml of a 30% (w/v) aqueous solution of sodium hydroxide are added while keeping the temperature at about 40° C. The product crystallizes by cooling to 2° C. and it is filtered, washed with water upon the filter and dried under vacuum. 64 Grams of d,l-N-acetyl-3,4-dimethoxyphenylalanine monohydrate are obtained with a yield of 90%.

EXAMPLE 8 d,l-2-acetamido-3-(3,4-dimethoxyphenyl)propionamide

62 Grams of d,l-2-acetamido-3-(3,4-dimethoxyphenyl) propionitrile are added to 100 ml of a 32% (w/v) aqueous solution of hydrochloric acid while keeping the temperature at 25° C. for about 1 hour, then 150 ml of of water and 100 ml of a 30% (w/v) aqueous solution of sodium hydroxide are added while keeping the temperature at 25° C. The suspension is then cooled to 2° C. and filtered. The solid is washed upon the filter with cold water and then dried under vacuum to give 63 g of product with a yield of 94.7%. A sample of product recrystallized from N,N-dimethylformamide shows m.p.=206°÷207° C.

EXAMPLE 9 d,l-N-acetyl-3,4-dimethoxyphenylalanine monohydrate 2.6 Grams of d,l-2-acetamido-3-(3,4-dimethoxyphenyl) propionamide are added under strong stirring to 50 ml of a 32% (w/v) aqueous solution of hydrochloric acid. The temperature of the reaction mixture goes up till about 55° C. and this temperature is kept for another 5 hours under strong stirring. Then the reaction mixture is diluted with 100 ml of water and added with 35 ml of a 30% (w/v) aqueous solution of sodium hydroxide. After cooling to 2° C., the product crystallizes and it is filtered, washed with water and dried under vacuum, so obtaining 26.2 g of d,l-N-acetyl-3,4-dimethoxyphenylalanine monohydrate with yield of 92%.

EXAMPLE 10 d,l-N-propionyl-3,4-dimethoxyphenylalanine

A suspension of 45.04 g of 3,4-dimethoxyphenylalanine in 340 ml of water is dissolved by adding a 30% (w/v) aqueous solution of sodium hydroxide up to pH 12. 29.2 Ml of propionic anhydride are added in about one hour while keeping the pH value at about 8 by means of a 30% (w/v) aqueous solution of sodium hydroxide. 24 Ml of a 32% (w/v) aqueous solution of hydrochloric acid are afterwards added and the aqueous phase is twice treated with 100 ml of trichloroethane. The trichloroethane washings are collected and extracted with 80 ml of water. The aqueous extract is washed with 50 ml of trichloroethane and then is collected to the aqueous phase. The aqueous solution is then acidified to pH 3 by means of a 32% (w/v) aqueous solution of hydrochloric acid and the product starts crystallizing. After about 30 minutes the mixture is further acidified to pH 2 and cooled to about 5° C. The crystallized solid is filtered, washed upon the filter first with water, then with toluene and lastly with petroleum ether so obtaining, after drying under vacuum, 44.1 g of product with a yield of 78.3%. A sample of product, further purified by crystallization from n-butyl acetate shows m.p.=142°-143° C.

EXAMPLE 11 d,l-N-carbomethoxy-3,4-dimethoxyphenylalanine

A mixture containing 45 g of 3,4-dimethoxyphenylalanine and 20 ml of a 30% (w/v) aqueous solution of sodium hydroxide in 200 ml of water is added with 17 ml of methyl chloroformate in about one hour while keeping the pH between 7 and 8 by means of an aqueous solution of sodium hydroxide and the temperature between 10° C. and 15° C. Afterwards, the reaction mixture is twice washed with 50 ml of methylene chloride and then is decolourized by means of 2.5 g of active charcoal and is filtered over dicalite. The filtrate is acidified to pH 2 by means of a 32% (w/v) aqueous solution of hydrochloric acid and the product is extracted once with 200 ml and twice with 75 ml of methylethylketone. The collected organic extracts are washed with 100 ml of a 10% (w/v) aqueous solution of sodium sulfate and then are dried over anhydrous sodium sulfate, decolourized by means of decolourizing earths and evaporated to dryness under vacuum. The residue is first crumbled and then crystallized from toluene. After filtration, washing with toluene and drying under vacuum, 45.8 g of pure product, having m.p.=116°÷117° C. are obtained, with a yield of 81%.

EXAMPLE 12 d,l-N-acetyl-3,4-dimethoxyphenylalanine-l-menthyl ester d,l+1,1

A mixture of 20.3 g of l-menthol and 24.82 g of d,l-N-acetyl-3-(3,4-dimethoxyphenyl)propionitrile in 100 ml of toluene is heated at 70° C. and is added in 30 minutes with a mixture of 5.2 ml of metansulfonic acid and of 3.6 ml of a 57% (w/v) aqueous solution of sulfuric acid. The reaction mixture is heated to the boiling for 5 hours and then water is eliminated from toluene by means of a suitable separator by boiling for other 2 hours. The reaction mixture is then cooled to about 85° C. and is added with 50 ml of water. The layers are separated, the aqueous phase is extracted with 20 ml of toluene and then is discarded while the toluene phases are collected and evaporated to dryness so obtaining an oily residue containing a racemic mixture of d,l- and l,l-N-acetyl-3,4-dimethoxyphenylalanine menthyl esters. The yield, calculated over the starting d,l-N-acetyl-3-(3,4-dimethoxyphenyl)propionitrile, is of about 95%.

EXAMPLE 13 d,l-N-acetyl-3,4-dimethoxyphenylalanine-l-menthyl ester [d,l+1,l]

A mixture of 100 g of d,l-N-acetyl-3,4-dimethoxyphenylalanine monohydrate, 71.2 g of l-menthol and 5.2 g of p-toluensulfonic acid in 350 ml of toluene is boiled under stirring for 5 hours while eliminating the water coming from the reaction by azeotropic distillation with a suitable separator. The amount of product obtained is determined by HPLC and results equal to 119.5 g with a yield of esterification of 84%.

EXAMPLE 14 d-N-acetyl-3,4-dimethoxyphenylalanine l-menthyl ester [d,l]

The reaction mixture coming from example 13 is slowly cooled under nitrogen atmosphere to about 65° C. and at this temperature the crystallization is seeded by adding a little amount of d-N-acetyl-3,4-dimethoxyphenylalanine l-menthyl ester. 7 Grams of potassium tert-butylate are added to the reaction mixture which is slowly cooled under stirring for 12 hours. Then 100 ml of water and 3.56 ml of acetic acid are added to the reaction mixture which is stirred for one hour and heated to 85° C. until complete solubilization. The solution is slowly cooled and at about 75° C. the crystallization is seeded by adding a little amount of d-N-acetyl-3,4-dimethoxyphenylalanine l-mentyl ester. The suspension is filtered at the temperature of about 20° C., the solid product is washed upon the filter with toluene and with water and lastly is dried under vacuum. 112.3 Grams of d-N-acetyl-3,4-dimethoxyphenylanine l-menthyl ester are obtained with a yield of 94% over the racemic mixture of the d,l-N-acetyl-3,4-dimethoxyphenylalanine l-menthyl ester and of 79% over the d,l-N-acetyl-3,4-dimethoxyphenylalanine monohydrate. The product shows m.p.=152°÷153° C. and $[\alpha]_D^{20} = -6.9°$ (c=1% in chloroform).

EXAMPLE 15 d,l-N-benzoyl-3,4-dimethoxyphenylalanine l-menthyl ester [d,l+l,l]

17.2 Grams of l-menthol and 1.8 g of p-toluensulfonic acid are added to a suspension of 32.93 g of d,l-N-benzoyl-3,4-dimethoxyphenylalanine in 300 ml of toluene and the reaction mixture is heated to the boiling for about 5 hours by eliminating the water of reaction by azeotropic distillation by means of a suitable separator. The reaction mixture is then cooled to about 50° C., once washed with 50 ml of water to eliminate the p-toluensulfonic acid and evaporated to dryness obtaining an oily residue containing 44.6 g of product, determined by HPLC, with a yield of 95%.

EXAMPLE 16 l-N-benzoyl-3,4-dimethoxyphenylalanine l-menthyl ester [l,l]

The d,l-N-benzoyl-3,4-dimethoxyphenylalanine l-menthyl ester coming from example 15 is diluted with 300 ml of toluene and the mixture is heated to boiling and dried by distilling off about 50 ml of solvent. Then the reaction mixture is cooled to about 65° C. and, under nitrogen atmosphere, is added with 2 g of potassium tert-butylate and 500 mg of d-N-benzoyl-3,4-dimethoxyphenylalanine l-menthyl ester. The reaction mixture is kept under stirring for about 8 hours by lowering the temperature first at room temperature and then to about 10° C. The suspension is then filtered and the obtained solid is washed on the filter first with water and then with toluene so obtaining, after drying under vacuum, 40.3 g of pure product with a yield of 90% calculated over the starting mixture of diastereoisomer esters. A sample of l-N-benzoyl-3,4-dimethoxyphenylalanine l-menthyl ester recrystallized by ethyl alcohol shows m.p.=146°÷147° C. and $[\alpha]_D^{20} = +11.3°$ (c=1% in chloroform).

EXAMPLE 17 d-N-propionyl-3,4-dimethoxyphenylalanine l-menthyl ester [d,l]

A mixture of 42.2 g of d,l-N-propionyl-3,4-dimethoxyphenylalanine, 26.95 g of l-menthol and 2.85 g of p-toluensulfonic acid in 180 ml of toluene is heated to the boiling under stirring for about 4 hours. The reaction mixture is then cooled, washed three times with 50 ml of water and dried by azeotropic distillation separating the water by means of a suitable separator. The dried toluene solution is cooled to 60° C., added with 0.84 g of potassium tert-butylate and then kept for 12 hours under stirring while cooling to room temperature. The resulting suspension is filtered and the obtained solid is recrystallized from toluene obtaining 38.7 g of product with a yield of 61.4%. The crystallized product shows m.p.=129°÷130° C. and $[\alpha]_D^{20} = -5.4°$ (c=1% in chloroform).

EXAMPLE 18 d-N-carbomethoxy-3,4-dimethoxyphenylalanine l-menthyl ester [d,l]

A mixture of 43.2 g of d,l-N-carbomethoxy-3,4-dimethoxyphenylalanine, 27 g of l-menthol and 3 g of p-toluensulfonic acid in 200 ml of toluene is heated to the boiling for 4 hours while eliminating the water coming from the reaction by means a suitable separator. The reaction mixture is cooled to about 50° C., washed three times with 50 ml of water and then it is heated again to the boiling, completely eliminating by distillation the water with a suitable separator. The reaction mixture is then cooled to room temperature under nitrogen atmosphere, added with 1.6 g of potassium tert-butylate and kept under stirring for 24 hours. The suspension is cooled to 0° C. and is filtered. The solid is dried and crystallized from methyl alcohol obtaining 45 g of product with a yield of 71%. The product shows m.p.=114°÷115° C. and $[\alpha]_D^{20} = -18.6°$ (c=1% in chloroform).

EXAMPLE 19

L-(−)-2-amino-3-(3,4-dihydroxyphenyl)propanoic acid

A mixture of 40.5 g of d-N-acetyl-3,4-dimethoxyphenylalanine l-menthyl ester, 20 ml of water, 20 ml of acetic acid and 35 ml of aqueous 48% (w/v) hydrobromic acid is heated to the boiling under stirring for 5 hours while distilling off the oily phase under vapour stream and recycling the condensed aqueous phase. Another 6 ml of 40% (w/v) aqueous hydrobromic acid are added to the reaction mixture which is heated to the boiling while distilling off vapour until the boiling temperature of the reaction mixture reaches 118° C., then the reaction mixture is heated at this temperature for other 6 hours. The reaction mixture is then cooled, diluted with 100 ml of water, decolourized on active charcoal and filtered on dicalite. The filtrate is brought to pH 4.5 by means of a 27% (w/v) aqueous solution of ammonium hydroxide and cooled to 5° C. obtaining an abundant precipitate which is filtered and washed on the filter first with water and then with acetone. After drying under vacuum at 40° C., 17.7 g of pure product are obtained with a yield of 89.8%. This product shows $[\alpha]_D^{13} = -12.9°$ (c=5.12% in 1N hydrochloric acid).

EXAMPLE 20

L-(−)-2-amino-3-(3,4-dihydroxyphenyl)propanoic acid

A mixture of 8.6 g of d-N-propionyl-3,4-dimethoxyphenylalanine l-menthyl ester, 8 ml of a 32% (w/v) aqueous solution of hydrochloric acid and 8 ml of a 50% (w/v) aqueous solution of hydrobromic acid is heated to the boiling for one hour and half and then the oily phase is distilled off while recycling the aqueous phase. The distillation is stopped after the temperature reaches 118° C. and the heating is continued for another 5 hours at this temperature. The reaction mixture is then cooled, diluted with 12.5 ml of water, decolourized on active charcoal and filtered on dicalite. The filtrate is brought to pH 4 by means of a 27% (w/v) aqueous solution of ammonium hydroxide and the suspension which forms is cooled to 5° C. for one hour. The precipitated solid is filtered, washed on the filter with water and acetone and dried under vacuum obtaining 3.6 g of pure levodopa having $[\alpha]_D^{13} = -12.9°$ (c=5.12% in 1N hydrochloric acid), with a yield of 89%.

EXAMPLE 21

L-(−)-2-amino-3-(3,4-dihydroxyphenyl)propanoic acid

A mixture of 11.7 g of l-N-benzoyl-3,4-dimethoxyphenylalanine l-mentyl ester and of 48 ml of a 48% (w/v) aqueous solution of hydrobromic acid is heated at the boiling for 4 hours and then is cooled to room temperature and diluted with 50 ml of water. The reaction mixture is extracted three times with 30 ml of methylene chloride and then is concentrated under vacuum. The residue is diluted with 60 ml of water and is brought to pH 4.5 by adding a 27% (w/v) aqueous solution of ammonium hydroxide. The obtained suspension is kept at 5° C. for about 1 hour and then is filtered and the solid is washed on the filter with water and acetone and dried under vacuum to give 3.7 g of product having $[\alpha]_D^{20} = -12.1°$ (c=5.12% in 1N hydrochloric acid). The yield is equal to 75%.

By operating in an analogous manner, the L-(−)-2-amino-3-(3,4-dihydroxyphenyl)propanoic acid is obtained starting from the d-N-carbomethoxy-3,4-dimethoxyphenylalanine l-menthyl ester.

We claim:

1. Process for the synthesis of optically active aminoacids of formula

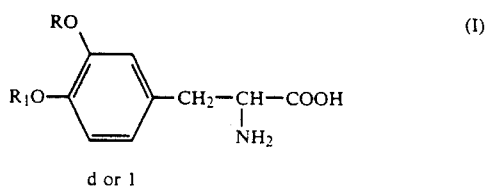

d or l wherein R and $R_1$, equal or different, represent a hydrogen atom or an alkyl radical, straight or branched, containing from 1 to 6 carbon atoms which comprises a) reacting compounds of formula

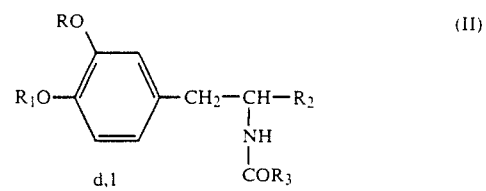

d,l wherein R and $R_1$ have the above seen meanings, $R_2$ represents a nitrile group or a COOH group and $R_3$ represents an alkyl or alkoxy radical, straight or branched, containing from 1 to 6 carbon atoms or an aryl radical, with an optically active alcohol of formula $$R_4\text{—OH} \qquad (III)$$

d or l wherein $R_4$ represents an alkyl or cycloalkyl radical, substituted or unsubstituted, containing from 3 to 12 carbon atoms, in an organic solvent immiscible with water, selected from the alkyl halides containing from 1 to 4 carbon atoms and the aromatic hydrocarbons, in presence of acids selected from aqueous or anhydrous sulfuric acid, alkyl sulfonic or arylsulfonic acids or mixtures thereof, at the boiling temperature of the reaction mixture, for a period of time comprised between about 2 and about 12 hours while eliminating the water coming from the reaction by means of an azeotropic distillation;

b) treating the resulting pair of diastereoisomer esters of formula

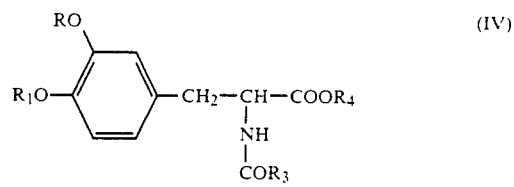

d,d + l,d or d,l + l,l wherein R, $R_1$, $R_3$ and $R_4$ have the above seen meanings, in an anhydrous organic solvent selected from the alkyl halides containing from 1 to 4 carbon atoms and the aromatic hydrocarbons with between about 0.05 and about 0.25 molar equivalents of a strong base selected from an alkali metal alcoholate containing from 1 to 6 carbon atoms, or an amide or hydride of an alkali metal, preferably under atmosphere of an inert gas at a temperature comprised between the room temperature and about 85° C. for a period of time comprised between about 4 and about 24 hours, preferably seeding the crystallization by means of crystals of the desired single diastereoisomer ester and lastly cooling at a temperature comprised between the room temperature and 0° C.;

c) treating the resulting single diastereoisomer ester of formula

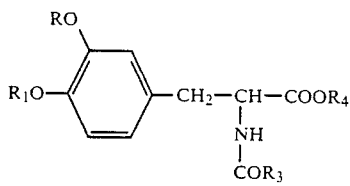

d, d or l, d or d, l or l, l wherein R, $R_1$, $R_3$ and $R_4$ have the above seen meanings, with aqueous solutions of hydrochloric or hydrobromic acid or of mixtures thereof at the boiling temperature of the reaction mixture for a period of time comprised between about 4 and about 24 hours to give the desired optically active aminoacid of formula (I).

2. Process according to claim 1 in which when one or both R and $R_1$ represent an alkyl radical, straight or branched, containing from 1 to 6 carbon atoms, the treatment in aqueous acid medium is prolonged up to the complete dealkylation of the compound of formula (V), to obtain the optically active aminoacid of formula (I) wherein $R=R_1=$ hydrogen.

3. Process according to claim 1 wherein the optically active alcohols of formula (III) are optically active cycloalkanols selected from d- and l-menthol, d- and l-borneol, d- and l-isomenthol, d- and l-neomenthol, d- and l-neoisomenthol, d- and l-1-cyclohexylethanol, d- and l-canfolalcohol, d- and l-isoborneol, d- and l-3-methylcyclopentanol.

4. Process according to claim 3 wherein l-menthol is the optically active cycloalkanol.

5. Process according to claim 1 wherein the reaction between the compounds of formula (II) and (III) is carried out in toluene.

6. Process according to claim 1 wherein in step b) the organic solvent is toluene and the strong base is potassium tert-butylate.

* * * * *